US00PP32218P2

(12) United States Plant Patent
NeSmith

(10) Patent No.: US PP32,218 P2
(45) Date of Patent: Sep. 22, 2020

(54) SOUTHERN HIGHBUSH BLUEBERRY PLANT NAMED 'TH-931'

(50) Latin Name: *Vaccinium corymbosum*
Varietal Denomination: TH-931

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/602,612

(22) Filed: Nov. 7, 2019

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

*Primary Examiner* — Keith O. Robinson
(74) *Attorney, Agent, or Firm* — Klarquist Sparkman, LLP

(57) ABSTRACT

The new variety 'TH-931' is provided. The new and distinct variety ripens around late May in south Georgia and early June in middle Georgia. The fruit of the new variety 'TH-931' are very large and firm. The new variety 'TH-931' exhibits high yields with an estimated chilling requirement of about 400 to 500 hours at or below approximately 7° C. The asexually reproduced variety is reliably propagated vegetatively.

6 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TH-931' is a southern highbush blueberry plant that is a *Vaccinium corymbosum.*

Variety denomination: The new southern highbush blueberry plant claimed is of the variety denominated 'TH-931'.

BACKGROUND OF THE INVENTION

The present invention relates to the discovery of a new and distinct cultivar of southern highbush blueberry plant botanically known as a *Vaccinium corymbosum* and herein referred to as 'TH-931', as herein described and illustrated.

The new blueberry plant variety 'TH-931' was selected in Griffin, Ga. in 2005. The new variety 'TH-931' ripens around late May in southern Georgia and early June in middle Georgia. The fruit of the new variety 'TH-931' are very large, with favorable firmness and good flavor. The new variety 'TH-931' has high yield and is vigorous with an estimated chilling requirement of about 400-500 hours at or below 7° C.

Pedigree and history: 'TH-931' was selected in 2005 at a plant experiment station in Griffin, Ga., originating from a cross of 'TH-622' (female parent, non-patented breeding selection) X 'Millennia' (male parent, U.S. Plant Pat. No. 12,816) made in 2002 by D. Scott NeSmith. The selection has been asexually propagated by vegetative stem cuttings and tested in plantings at blueberry research farms in Alapaha and Griffin, Ga. since 2007.

SUMMARY OF THE INVENTION

The new blueberry plant variety 'TH-931' has not been observed under all possible environmental conditions. The phenotype may vary somewhat with variations in environment and cultural practices such as temperature and light intensity without, however, any variance in genotype.

The following traits have been repeatedly observed in plants of the 'TH-931' variety growing at Alapaha and Griffin, Ga., and are determined to be the unique characteristics of the new blueberry plant variety 'TH-931':

1. Mid to late ripening;
2. High yield;
3. Very large berry size;
4. Good berry color; and
5. Favorable berry firmness.

The new variety 'TH-931' can be compared to the mid to late ripening southern highbush blueberry varieties 'Star' (U.S. Plant Pat. No. 10,675) and 'Camellia' (U.S. Plant Pat. No. 18,151).

Comparison: The 'TH-931' variety is mid to late season, and begins ripening after the mid-to-late season varieties 'Camellia' and 'Star' in south and middle Georgia. 'TH-931' has large, very firm berries with good flavor as compared to 'Star' and 'Camellia' at Alapaha, Ga. (Table 1) and at Griffin, Ga. (Table 2). Table 3 describes yield, berry weight, firmness and Brix for 'TH-931' as compared to the 'Star' and 'Camellia' southern highbush blueberry cultivars for the years 2010 thru 2013. 'TH-931' had larger yields and berry weight than either 'Star' or 'Camellia'. 'TH-931' has a two-year average Brix lower than the 'Star' or 'Camellia' cultivars. The female parent, 'TH-622' is an old breeding selection that no longer exists. However, comparing past performances of 'TH-931' to 'TH-622' demonstrated that the chilling requirement for 'TH-931' (400-500 hours) is lower than 'TH-622' (550 to 600 hours), but higher than the male parent 'Millennia' (250 to 350 hours). 'TH-931' flowering time (March 16 on average) is well before 'TH-622' (March 28 to April 2 on average), but after 'Millennia' (February 25 to March 5 on average). Ripening time of 'TH-931' (May 21 on average) is before 'TH-622' (May 25 to June 1 on average), and later than 'Millennia' (May 1 to May 8 on average). Fruit development period for 'TH-931' (66 days average) is similar to 'TH-622' and 'Millennia' (65 days on average). Berry color for 'TH-931' averages 8.1/10, whereas 'TH-622' averages 8.5/10 and 'Millennia' averages 7.2/10. Berry firmness and flavor are similar to 'TH-622' and 'Millennia'.

TABLE 1

5-year average ratings of some fruit and plant characteristics of 'TH-931' and standard cultivars 'Star' and 'Camellia' from 2009 thru 2013 in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in 2007.

| Berry and | Alapaha location | | |
|---|---|---|---|
| plant attributes[1/] | 'Star' | 'Camellia' | 'TH-931' |
| Berry size | 7.6 ± 0.2 | 8.9 ± 0.2 | 8.8 ± 0.2 |
| Berry scar | 7.0 ± 0.1 | 7.2 ± 0.2 | 7.7 ± 0.3 |
| Berry color | 7.1 ± 0.1 | 8.7 ± 0.2 | 8.1 ± 0.4 |
| Berry firmness | 7.2 ± 0.1 | 7.2 ± 0.1 | 7.5 ± 0.2 |
| Berry flavor | 7.0 ± 0.1 | 7.8 ± 0.1 | 7.5 ± 0.2 |
| Cropping | 4.7 ± 1.7 | 5.4 ± 0.3 | 4.6 ± 0.9 |
| Plant vigor | 6.3 ± 0.2 | 9.8 ± 0.2 | 7.0 ± 0.2 |
| Date of 50% flowering | Mar. 3 | Mar. 11 | Mar. 16 |
| Date of 50% ripening | May 8 | May 15 | May 21 |
| Fruit development period (days) | 66 ± 6.1 | 65 ± 4.9 | 66 ± 4.2 |

[1/]Values are means + the standard error with n = 5.

TABLE 2

5-year average ratings of some fruit and plant characteristics of 'TH-931' and standard cultivars 'Star' and 'Camellia' from 2009 thru 2013 in field test plots at Griffin, GA. Rating scales are based on a 1 to 10 score, with 1 being the least desirable and 10 being the most desirable. A value of 6-7 is generally considered to be the minimum acceptable rating for a commercial cultivar. These plants were established in 2007.

| Berry and | Griffin location | | |
|---|---|---|---|
| plant attributes[1/] | 'Star' | 'Camellia' | 'TH-931' |
| Berry size | 7.4 ± 0.2 | 8.6 ± 0.2 | 8.9 ± 0.1 |
| Berry scar | 6.9 ± 0.1 | 7.0 ± 0.1 | 7.8 ± 0.2 |
| Berry color | 7.1 ± 0.1 | 7.9 ± 0.2 | 8.8 ± 0.3 |
| Berry firmness | 7.2 ± 0.1 | 7.2 ± 0.1 | 7.4 ± 0.2 |
| Berry flavor | 7.1 ± 0.1 | 7.4 ± 0.2 | 7.6 ± 0.2 |
| Cropping | 6.8 ± 1.1 | 7.9 ± 0.2 | 6.2 ± 0.3 |
| Plant vigor | 8.5 ± 0.3 | 9.8 ± 0.1 | 8.5 ± 0.3 |
| Date of 50% flowering | Mar. 13 | Mar. 25 | Mar. 27 |
| Date of 50% ripening | May 25 | May 31 | Jun. 3 |
| Fruit development period (days) | 73 ± 10.4 | 67 ± 4.8 | 68 ± 2.5 |

[1/]Values are means + the standard error with n = 5.

TABLE 3

Multi-year average yield, berry weight, firmness, and Brix for 'Star', 'Camellia', and 'TH-931' cultivars grown in Griffin, GA between 2010 and 2013

| Year | 'Star' | 'Camellia' | 'TH-931' |
|---|---|---|---|
| | Yield (lbs/bush)[1/] | | |
| 2011 | 12.7 ± 3.6 | 9.7 ± 0.9 | 13.3 ± 1.6 |
| 2012 | 11.7 ± 2.3 | 10.5 ± 0.8 | 22.0 ± 1.5 |
| 2013 | 3.9 ± 0.6 | 15.9 ± 1.0 | 21.0 ± 0.6 |
| Avg | 9.4 | 12.0 | 18.8 |
| | Berry wt. (g/berry)[2/] | | |
| 2010 | 1.53 ± 0.09 | 2.94 ± 0.12 | 3.36 ± 0.18 |
| 2011 | 1.20 ± 0.04 | 1.97 ± 0.11 | 3.29 ± 0.10 |
| 2012 | 1.80 ± 0.07 | 1.60 ± 0.09 | 2.66 ± 0.08 |
| 2013 | 1.79 ± 0.06 | 2.56 ± 0.10 | 2.92 ± 0.04 |
| Avg | 1.58 | 2.28 | 3.06 |
| | Firmness (g/mm)[2/] | | |
| 2010 | 196 ± 4 | 150 ± 2 | 198 ± 4 |
| 2011 | 206 ± 6 | 166 ± 3 | 196 ± 2 |
| 2012 | 190 ± 5 | 164 ± 4 | 193 ± 5 |
| 2013 | 191 ± 5 | 150 ± 2 | 181 ± 2 |
| Avg | 196 | 157 | 191 |
| | Brix (%)[3/] | | |
| 2012 | 13.9 ± 0.6 | 14.5 ± 0.4 | 11.3 ± 0.5 |
| 2013 | 13.5 ± 0.5 | 13.3 ± 0.3 | 10.7 ± 0.3 |
| Avg | 13.7 | 13.9 | 11.0 |

[1/]Values are means + the standard error with n = 3.
[2/]Values are means + the standard error with n = 3 (each sample derived from 25 berry avg).
[3/]Values are means + the standard error with n = 3 (each sample derived from 5 berry composite),

BRIEF DESCRIPTION OF THE DRAWINGS

The accompanying photographic illustrations show typical specimens in full color of the foliage, flowering, and fruit of the new variety 'TH-931'. The colors are as nearly true as is reasonably possible in a color representation of this type. The age of the plants depicted in the photographs is between five and six years old. The observations for TH-931 presented here have only been made in a temperate climate. Therefore, dormancy occurs and fruiting is only on one year old shoots. The environment is not conducive to seeing flowering and fruiting on current season shoots.

DETAILED BOTANICAL DESCRIPTION

Figure 1:
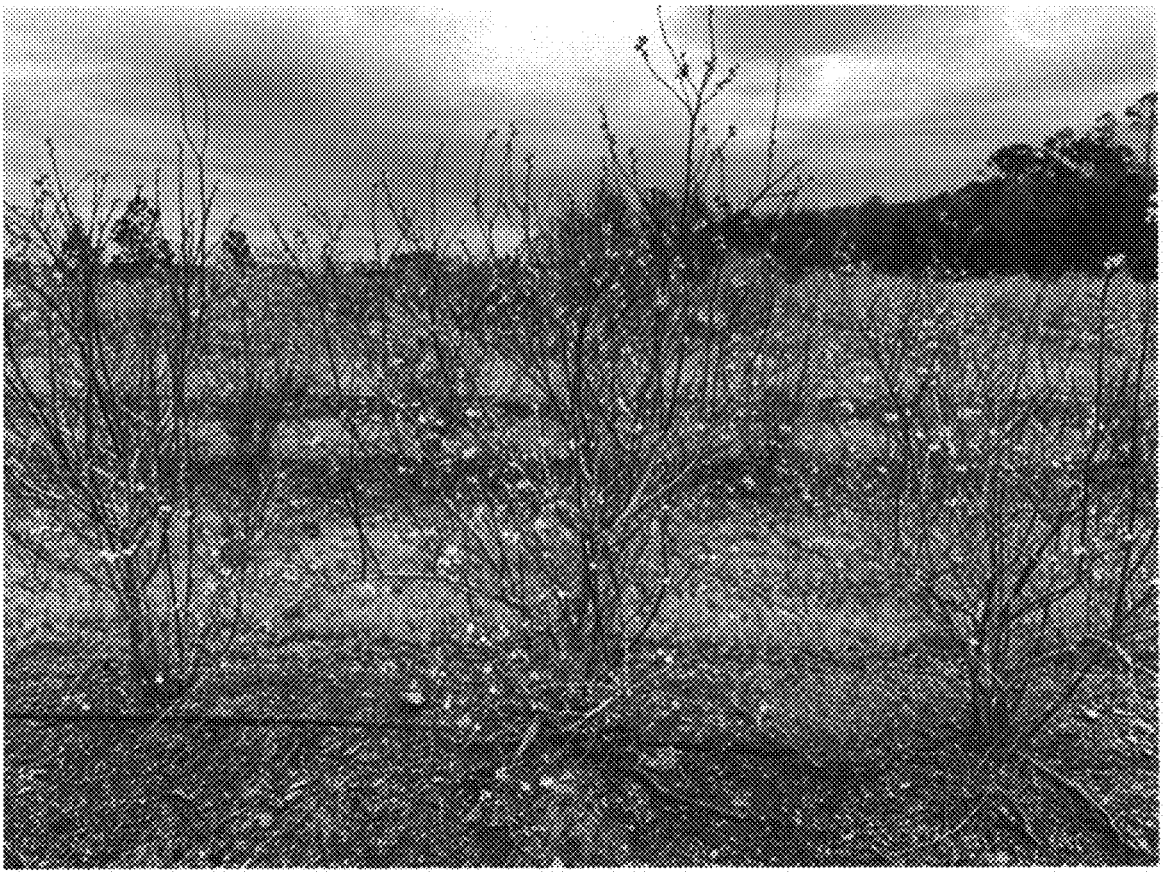
FIG. 1 is a photograph of the new variety 'TH-931' during flowering in Alapaha, Ga.
Figure 2:
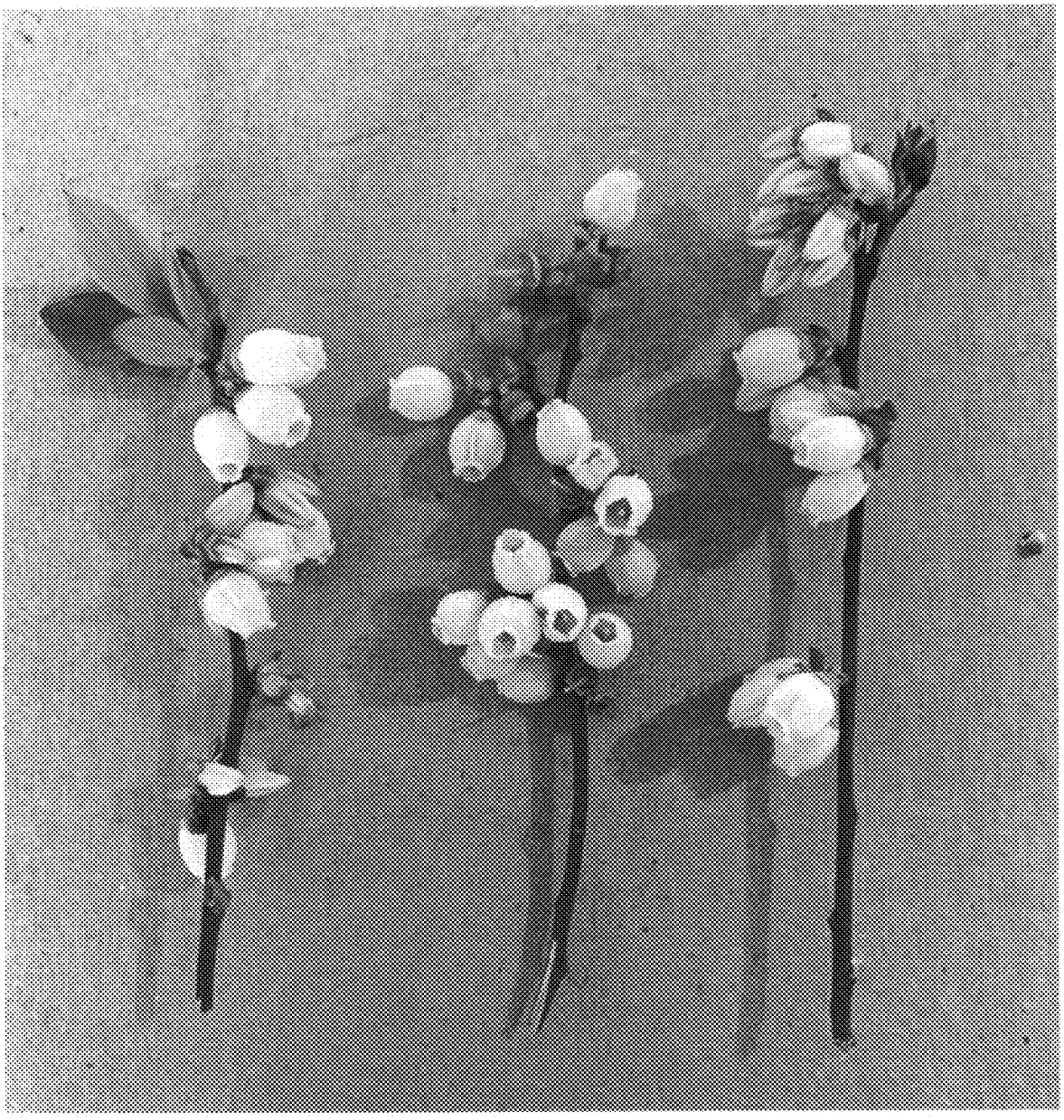
FIG. 2 is a close up photograph of the new variety 'TH-931' during flowering in Alapaha, Ga.
Figure 3:
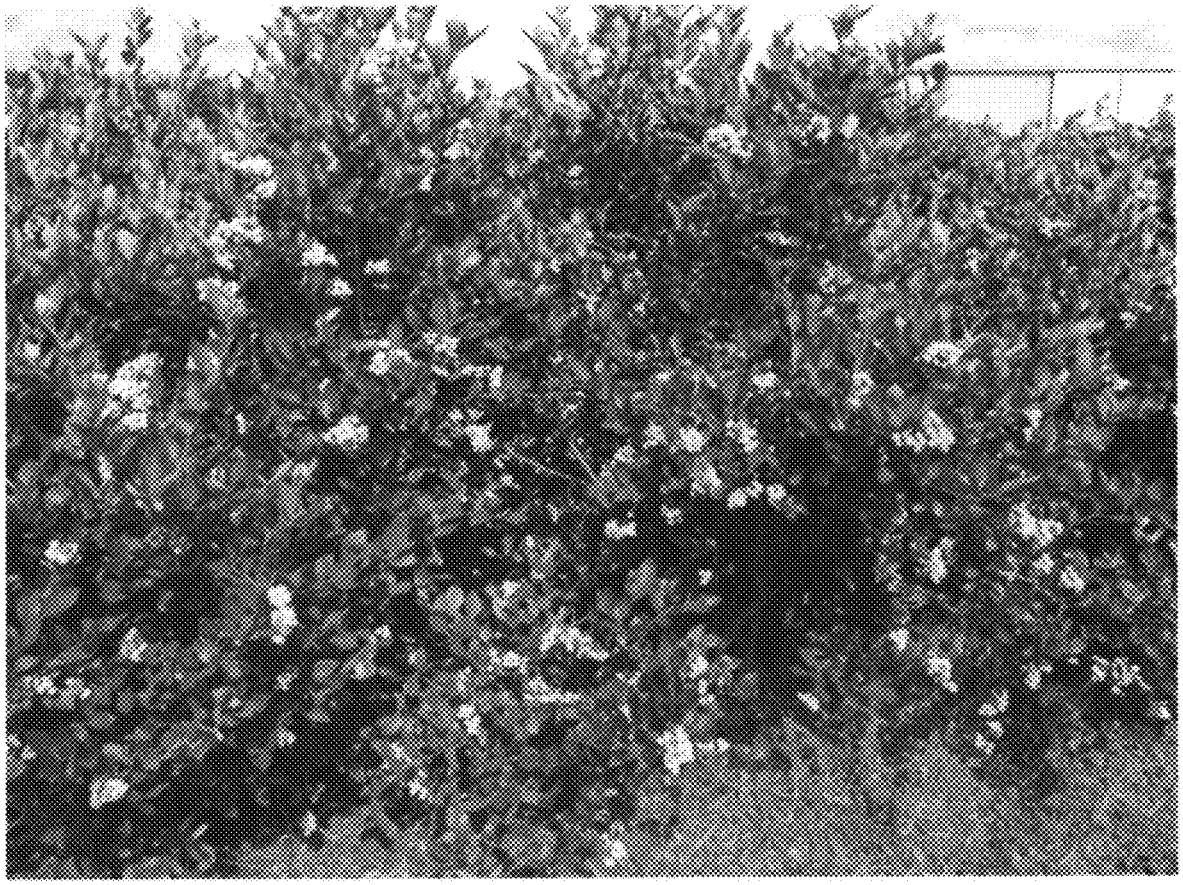
FIG. 3 is a photograph of the new variety 'TH-931' during fruit ripening in Alapaha, Ga.
Figure 4:
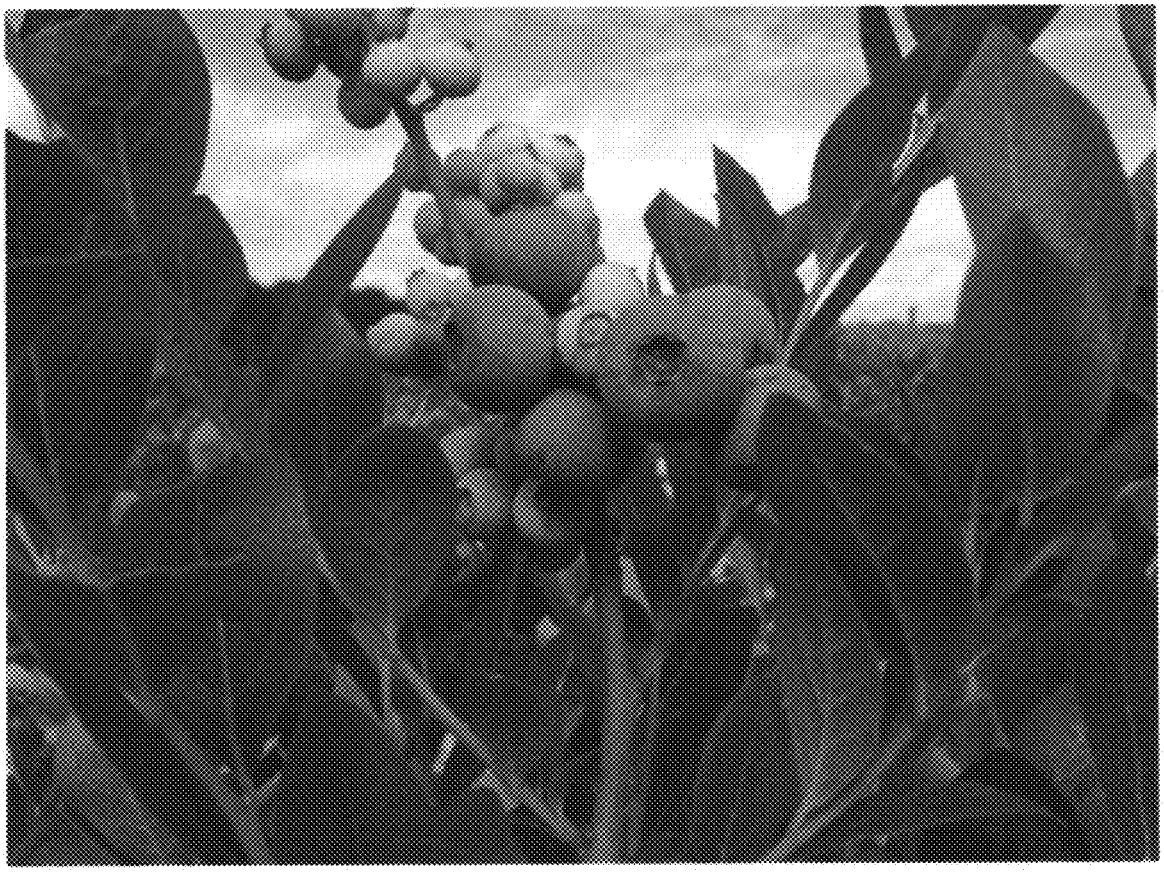
FIG. 4 is close up photographs of new variety 'TH-931' fruit clusters.
Figure 5:
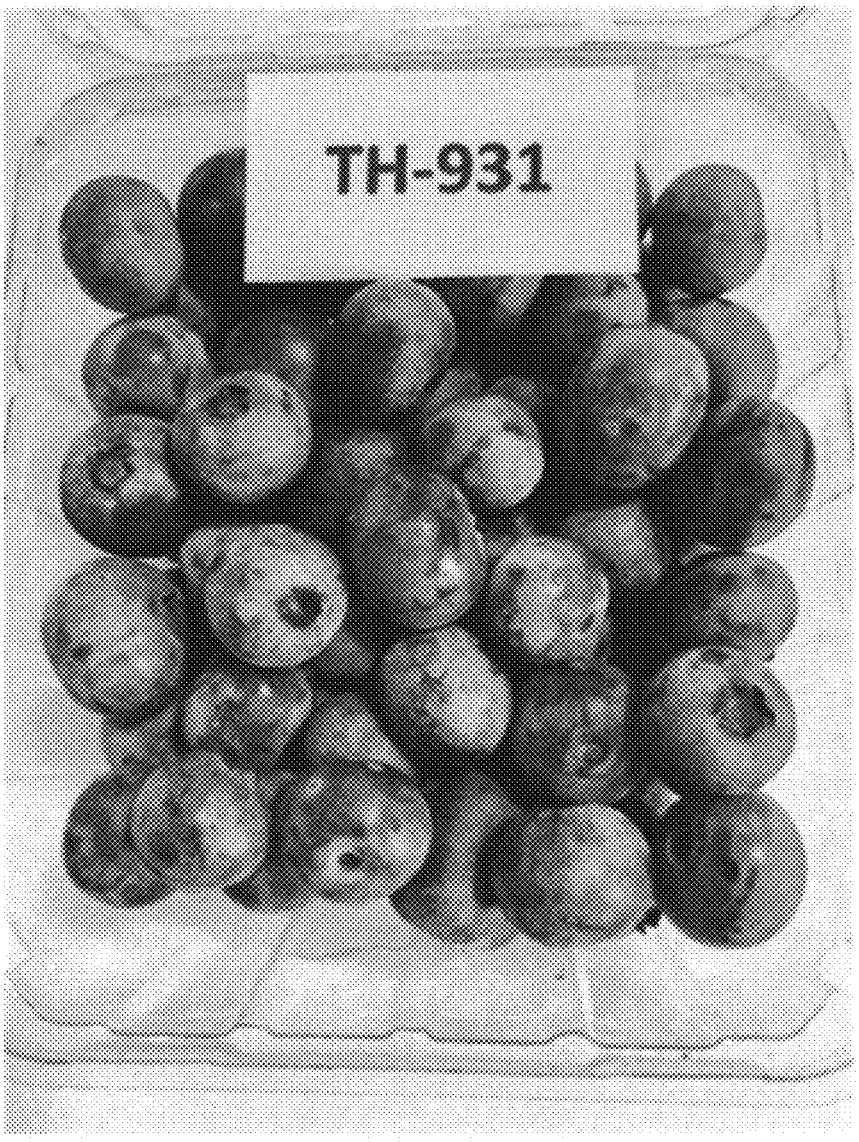
FIGS. 5 and 6 are photographs of harvested fruit of the new variety 'TH-931'
Figure 6:
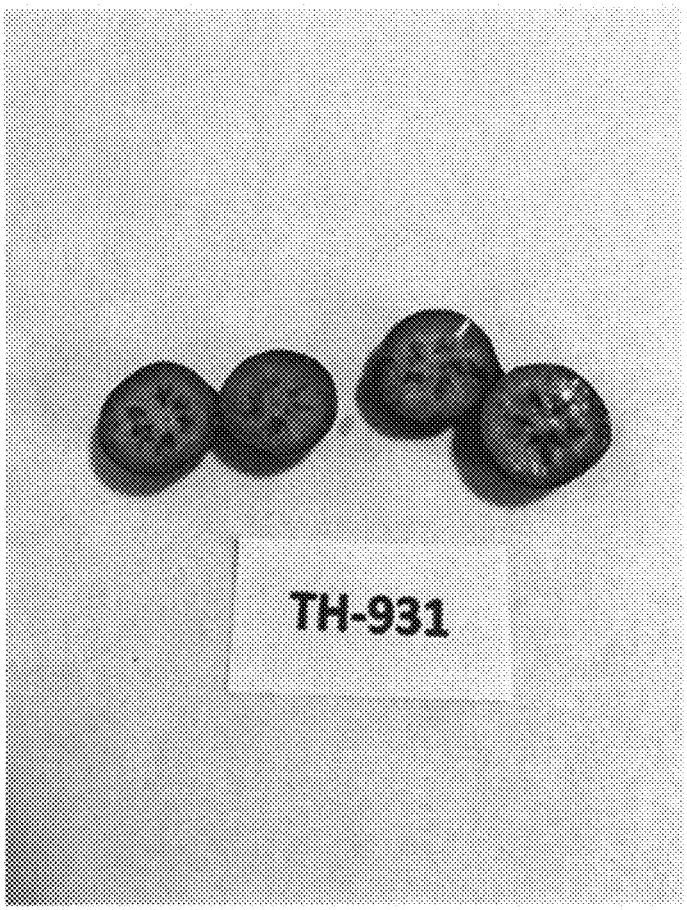

Throughout this specification, color names beginning with a small letter signify that the name of that color, as used in common speech, is aptly descriptive. Color names beginning with a capital letter designate values based upon The R.H.S. Colour Chart, $5^{th}$ edition published in 2007 by The Royal Horticultural Society, London, England.

The following is a detailed description of the botanical and pomological characteristics of the new variety 'TH-931'. Where dimensions, sizes, colors, and other characteristics are given, it is to be understood that such characteristics are approximations and averages set forth as accurately as practicable. The descriptions reported herein are largely from four to six year old specimen plants grown in Alapaha and Griffin, Ga., with supplemental irrigation.

Plant:

*Size.*—1.5 to 1.8 m tall by 4 years. Plants grown under highly productive soil and fertility conditions have exceeded 1.8 m tall in 4 years. The plant crown, or base, is medium, typically 25 to 35 cm in diameter. Upper portion of plant canopy reaches 1.3 to 1.5 m in diameter by 3 to 4 years.

*Growth habit.*—Mostly upright to semi-spreading, with 3 to 5 main canes arising from the crown within 10 cm of the soil surface.

*Growth.*—Moderately vigorous.

*Productivity.*—High to very high crop yield, averaging 13 to 21 lbs of fruit per plant each year for plants 4 years and older grown under well fertilized and irrigated field conditions.

*Hardiness.*—Has been grown in Alaphaha, Ga., USDA hardiness zone 8a; and in Griffin, Ga., USDA hardiness zone 8a; similar to other southern highbush varieties such as 'Camellia' (U.S. Plant Pat. No. 18,151).

*Chilling requirement.*—400 to 500 hours, more or less, of temperatures at or below 7° C. to induce normal leafing and flowering during the spring under conventional dormant production systems. The chill requirement is more than the male parent 'Millennia' (U.S. Plant Pat. No. 12,816; 250 to 350 hours of chilling required), and more similar to the female parent 'TH-622' (non-patented breeding selection; 450 to 550 hours of chilling required).

*Leafing.*—Plants tend to break sufficient leaf buds simultaneously with, or shortly after, anthesis.

*Fruiting wood.*—5-10 twigs 15 to 25 cm in length, with internode lengths of 15 to 20 mm common.

*Canes.*—Diameter: Main cane base diameter 30 to 50 mm, two year old cane diameter 15 to 20 mm, current season wood diameter 5 to 10 mm. Color: Main cane color most near Brown N200B, two year old cane transitions from Greyed Orange 165B to Grey 201B. Yellow Green 145C in current season wood.

*Disease and pest resistance.*—No exceptional disease and pest resistance or susceptibility observed. Typical for southern highbush 'Camellia' cultivars.

Foliage:

*Leaf color.*—Healthy mature leaves. Top side: Green 137A to Green N137A. Under side: Green 138C.

*Leaf arrangement.*—Alternate, simple.

*Leaf shape.*—Elliptic.

*Leaf surface.*—Glaucous, upper and lower.

*Leaf margins.*—Nearly entire.

*Leaf venation.*—Pinnate with slight netting.

*Leaf apices.*—Broadly acute.

*Leaf bases.*—Acute.

*Leaf dimensions.*—Length: 50.0 to 60.0 mm. Width: 30.0 to 35.0 mm.

*Petioles.*—Small. Length: 3.5 to 4.5 mm. Width: 1.5 to 2.0 mm. Color: Yellow-Green 145B.

Flowers:

*Date of* 50% *anthesis.*—March 16 in southeast Georgia; March 27 in middle Georgia (5 year average).

*Flower shape.*—Urceolate.

*Flower bud number.*—Medium to high, averaging 3 to 6 buds per fruiting shoot.

*Vegetative bud burst.*—Beginning flowering for TH-931 on 1 year old shoots is March 5 to 15 on average. Leaf bud burst occurs nearer 50% flowering, or March 15 to 20 on average for first leaf buds.

*Flowers per cluster.*—5 to 7.

*Flower fragrance.*—None.

*Corolla tube.*—Color: White NN 155B to White 155C. Length: 9.0 to 10.0 mm. Width: 7.0 to 8.0 mm. Aperture width: 4.0 to 4.5 mm. Anthocyanin Coloration: medium to strong in early stages of bud development, but mostly absent in nearly open or entirely open corollas.

*Flower peduncle.*—Length: 8.0 to 10.0 mm. Color: Yellow Green 145B.

*Flower pedicle.*—Length: 0.5 to 2.0 mm. Color: Green 138B.

*Calyx* (*with sepals*).—Diameter: 7.0 to 8.0 mm. Color: Green 138B.

*Stamen.*—Length: 4.0 to 4.5 mm. Number per flower: 10. Filament color: Green White 157B.

*Style.*—Length: 8.0 to 9.0 mm. Color: Yellow Green 145B.

*Pistil.*—Length: 12.0 to 14.0 mm. Ovary color (exterior): Green 138B.

*Anther.*—Length: 4.5 to 5.5 mm. Number: 10. Color: Greyed-Orange 165B.

*Pollen.*—Abundance: High. Color: Yellow-White 158B.

*Self-compatibility.*—The cultivar has a moderate degree of self-compatibility.

Fruit:

*Date of* 50% *maturity.*—May 21 in southeast Georgia; June 3 in middle Georgia (5 year average).

*Fruit development period.*—66 to 68 days.

*Fruit bloom intensity.*—Medium to strong.

*Berry color.*—With wax: Violet Blue 97B. With wax removed: Black 202A.

*Berry surface wax abundance.*—Medium to high.

*Berry flesh color.*—Green White 157B.

*Berry weight.*—First harvest: 3.5 to 5.0 g. Second harvest: 2.5 to 3.5 g.

*Berry size.*—Height from calyx to scar: 15.0 to 18.0 mm. Diameter: 18.0 to 23.0 mm.

*Berry shape.*—Nearly spherical.

*Fruit stem scar.*—Medium, dry, with no tearing upon harvest.

*Calyx.*—Depth shallow, 1.5 to 2.5 mm; width 5.0 to 7.0 mm; sepals occasionally present, inward when present, <1 mm.

*Berry firmness.*—Good to very good.

*Berry flavor and texture.*—Flavor sharply (high) acidic flavor, mild sweetness; smooth texture.

*Storage quality.*—Very good.

*Suitability for mechanical harvesting.*—Not likely suitable.

*Uses.*—Primarily to be used as fresh fruit for shipping and processing markets.

*Infructescence* (*fruit clusters*).—Medium density or "looseness".

Seed:

*Seed abundance in fruit.*—Medium to high, with 10 to 20 (or more) fully developed seeds per berry.

*Seed color.*—Greyed-Orange 165B.

*Seed dry weight.*—55.6 mg per 100 seed.

*Seed size.*—1.8 to 2.1 mm long.

What is claimed is:

1. A new and distinct variety of southern highbush blueberry plant named 'TH-931', as illustrated and described herein.

* * * * *